US010056091B2

(12) United States Patent
Orescanin et al.

(10) Patent No.: US 10,056,091 B2
(45) Date of Patent: Aug. 21, 2018

(54) MICROPHONE ARRAY BEAMFORMING

(71) Applicant: Bose Corporation, Framingham, MA (US)

(72) Inventors: Marko Orescanin, Salinas, CA (US); Mehmet Ergezer, Newton, MA (US)

(73) Assignee: Bose Corporation, Framingham, MA (US)

( * ) Notice: Subject to any disclaimer, the term of this patent is extended or adjusted under 35 U.S.C. 154(b) by 0 days.

(21) Appl. No.: 15/400,332

(22) Filed: Jan. 6, 2017

(65) Prior Publication Data

US 2018/0197559 A1 Jul. 12, 2018

(51) Int. Cl.

| | |
|---|---|
| ***A61F 11/06*** | (2006.01) |
| ***G10L 21/0232*** | (2013.01) |
| ***H04R 1/40*** | (2006.01) |
| ***H04R 1/10*** | (2006.01) |
| *G10L 21/0216* | (2013.01) |

(52) U.S. Cl.

CPC ........ *G10L 21/0232* (2013.01); *H04R 1/1016* (2013.01); *H04R 1/1058* (2013.01); *H04R 1/406* (2013.01); *G10L 2021/02166* (2013.01)

(58) Field of Classification Search

USPC ....... 381/26, 58, 61, 71.6, 71.8, 91, 92, 111, 381/122

See application file for complete search history.

(56) References Cited

U.S. PATENT DOCUMENTS

| | | | | |
|---|---|---|---|---|
| 2008/0201138 | A1* | 8/2008 | Visser | G10L 21/0208 704/227 |
| 2013/0054231 | A1 | 2/2013 | Jeub et al. | |
| 2013/0083934 | A1* | 4/2013 | hgren | G10K 11/34 381/58 |
| 2016/0293179 | A1* | 10/2016 | Thiergart | H04R 3/005 |

FOREIGN PATENT DOCUMENTS

| | | |
|---|---|---|
| WO | 2005/004532 A1 | 1/2005 |
| WO | 2016/090342 A2 | 6/2016 |

OTHER PUBLICATIONS

Brandstein, M., Ward, D. (Eds.), Microphone Arrays, Signal Processing Techniques and Applications, Chapter 2, pp. 19-38; Superdirective Microphone Arrays, Springer-Verlag, Germany, 2001.

Brandstein, M., Ward, D. (Eds.), Microphone Arrays, Signal Processing Techniques and Applications, Chapter 4, pp. 61-85; Spatial Coherence Functions for Differential Microphones in Isotropic Noise Fields, Springer-Verlag, Germany, 2001.

(Continued)

*Primary Examiner* — Yosef K Laekemariam

(74) *Attorney, Agent, or Firm* — Brian M. Dingman; Dingman IP Law, PC

(57) ABSTRACT

A system that includes a microphone array comprising a plurality of microphones positioned at different locations, where the microphones output microphone signals. A beamformer is applied to the microphone output signals and is configured to control a gain that is applied to the microphone (Continued)

output signals. The gain is frequency dependent and is related to a mismatch in sensitivity between two or more of the microphones.

19 Claims, 5 Drawing Sheets

(56) References Cited

OTHER PUBLICATIONS

The International Search Report and the Written Opinion of the International Searching Authority dated Mar. 13, 2018 for PCT Application No. PCT/US2018/012511.
Simon Doclo, et al: "Superdirective Beamforming Robust Against Microphone Mismatch", IEEE Transactions on Audio, Speech and Language Processing, IEE, vol. 15, No. 2, Feb. 1, 2007, pp. 617-631, XP011157501, ISSN:: 1558-7916, DOI: 10.1109/TASL. 2006.881676.

* cited by examiner

MICROPHONE ARRAY BEAMFORMING

BACKGROUND

This disclosure relates to microphone array beamforming.

Beamforming can control the gain that is applied to the outputs of individual microphones or microphones in an array. While in some applications it is preferable to maximize the microphone array gain from beamforming, increasing the gain can also increase the internal or self-noise of the system particularly in applications where the microphones are in close proximity to each other. This noise is also referred to as spatially uncorrelated noise. In speech communication applications, noise reduces the effectiveness of the communication.

SUMMARY

All examples and features mentioned below can be combined in any technically possible way.

In one aspect, a system includes a microphone array comprising a plurality of microphones positioned at different locations, where the microphones output microphone signals. A beamformer is applied to the microphone output signals and is configured to control a gain that is applied to the microphone output signals, where the gain is frequency dependent and is related to a mismatch in sensitivity between two or more of the microphones.

Embodiments may include one of the following features, or any combination thereof. The microphones may be part of headphones. In one non-limiting example, the headphones comprise an in-ear headset, and the microphones are constructed and arranged to detect a sound field that is external to the headset. The beamformer may be configured to reduce the gain that is applied to the microphone output signals more at lower input frequencies than at higher input frequencies. The gain may contribute to microphone white noise gain, and the reduced gain may result in a reduction of white noise gain. The white noise gain reduction is in one non-limiting example at least about 4 dB over a range of input frequencies, which may be up to about 300 Hz.

Embodiments may include one of the following features, or any combination thereof. The beamformer may be super-directive. The beamformer may be characterized by a plurality of frequency domain coefficients. The frequency domain coefficients may be based on at least one of a coherence function of a diffuse noise field, and a power spectral density (PSD) matrix of a non-diffuse noise field. The coherence function may be based on microphone sensitivity mismatch parameters of the microphones of the array. The microphone sensitivity mismatch parameters may in one non-limiting example be between approximately 0.1 dB and approximately 0.3 dB. The beamformer may be either a near-field beamformer or a far-field beamformer. The beamformer may be a minimum variance distortionless response (MVDR) beamformer.

In another aspect, a system includes a microphone array comprising a plurality of microphones positioned at different locations, where the microphones output microphone signals. A beamformer is applied to the microphone output signals and is configured to reduce a gain that is applied to the microphone output signals more at lower input frequencies than at higher input frequencies, wherein the gain contributes to array white noise gain, and wherein the reduced gain results in a reduction of white noise gain.

Embodiments may include one of the above and/or below features, or any combination thereof. The microphones may be part of headphones. The beamformer may be super-directive. The beamformer may be characterized by a plurality of frequency domain coefficients. The frequency domain coefficients may be based on at least one of a coherence function of a diffuse noise field and a power spectrum density of a non-diffuse noise field. The coherence function may be based on microphone sensitivity mismatch parameters of the microphones of the array. The beamformer may be a minimum variance distortionless response (MVDR) beamformer.

DETAILED DESCRIPTION

Speech communication applications typically employ an array of microphones to capture speech. The microphone array can be part of a headphone or headset, or a loudspeaker, for example. In many use situations, the microphones also capture unwanted noise. Beamforming can be used to focus the array on the source of the speech, and thereby increase the signal to noise ratio. Some types of beamformers are particularly sensitive to internal microphone noise, which is spatially uncorrelated noise. The microphone array gain is an indicator of the performance of the beamformer as a function of frequency. One goal of a beamformer is to maximize the array gain. Another goal is to minimize spatially uncorrelated noise, or system noise, while maintaining a high array gain. In the literature this is referred to as minimizing white noise gain (WNG).

Beamformers suppress spatially correlated noise, but can amplify spatially uncorrelated noise, which is not desirable. The microphone array beamformers described herein are configured to accomplish frequency-dependent microphone gain control, where the gain control is related to sensitivity mismatches between microphones in the microphone array. A result is an optimum beamforming in the presence of spatially uncorrelated noise (or system noise), over at least some frequencies, and thus improved speech communication results. The term "white noise gain" (WNG) is used at times herein to describe a quantity that relates to the ability of a beamformer to suppress spatially uncorrelated noise.

Figure 1:
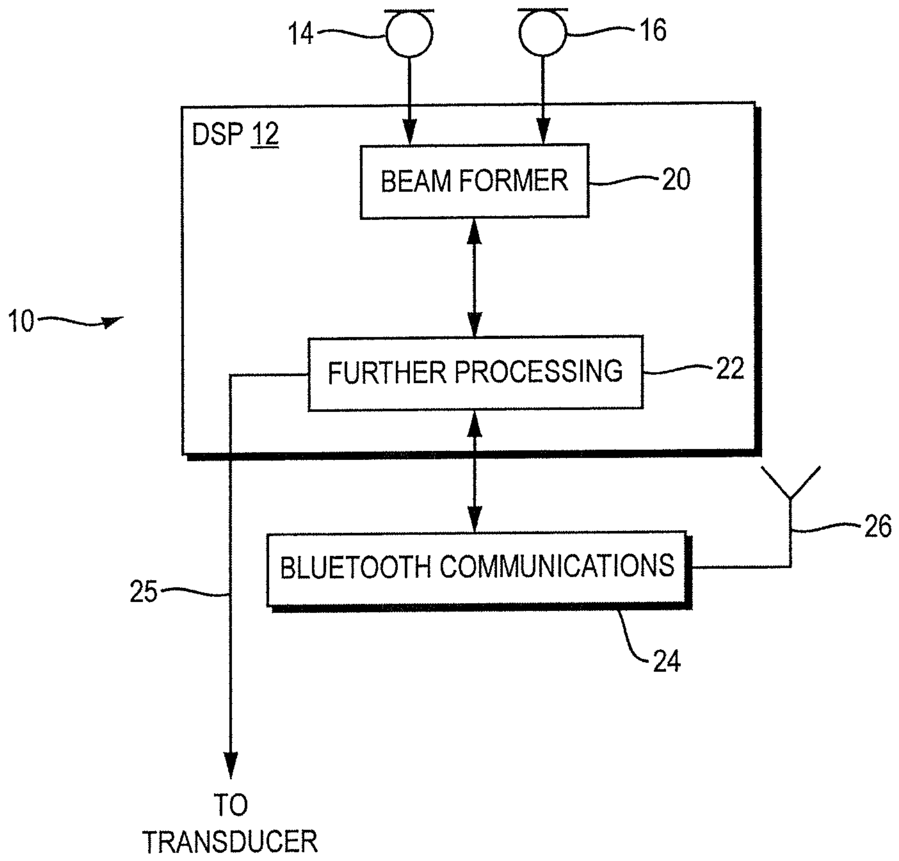
FIG. 1 is schematic block diagram of an audio device that includes a microphone array beamformer.

FIG. 1 is schematic block diagram of an audio device 10 that includes an example of the present microphone array beamforming. Standard components and functions of audio devices such as wireless headphones and speakers (e.g., A/D, D/A, amplification, and audio signal processing) are not included in FIG. 1, for the sake of clarity. Audio device 10 has multiple microphones—two in this non-limiting example, microphones 14 and 16. Digital signal processor (DSP) 12 receives the digitized and amplified microphone outputs. DSP 12 includes code that accomplishes beamformer 20 that is applied to the microphone output signals. Beamforming in general is known in the art. Superdirective microphone array beamforming is described in: Joerg Bitzer, K. U. Simmer, "Superdirective Microphone Arrays," in *Microphone Arrays*, Springer Berlin Heidelberg, 2001, chapters 2 and 4 on pp. 19-38 and 61-85, the disclosure of which is incorporated herein by reference in its entirety. Superdirective beamformers can be derived by applying the minimum variance distortionless responses (MVDR) principle to diffuse noise fields.

The beamformed outputs are typically subjected to further processing 22, as would be apparent to one skilled in the art. Such further processing may include, but not be limited to, mixing, audio adjustment, acoustic echo cancellation, noise suppression, equalization, and/or gain compensation. Processed audio output signals can be provided to one or more electro-acoustic transducers as indicated by output 25, for example to the electro-acoustic transducers of headphones. For wireless audio devices, the beamformed, processed microphone inputs can be provided to wireless communications module 24 that has antenna 26, which is adapted to send (and as needed receive from an audio source such as a smartphone) wireless signals via a wireless connection, such as a Bluetooth® connection. While Bluetooth® is used as an example of the wireless connection, other communication protocols may also be used. Some examples include Bluetooth® Low Energy (BLE), Near Field Communications (NFC), IEEE 802.11, or other local area network (LAN) or personal area network (PAN) protocols. Outbound and inbound communications can also be provided over wires or any other communication medium or technology.

Figure 2:
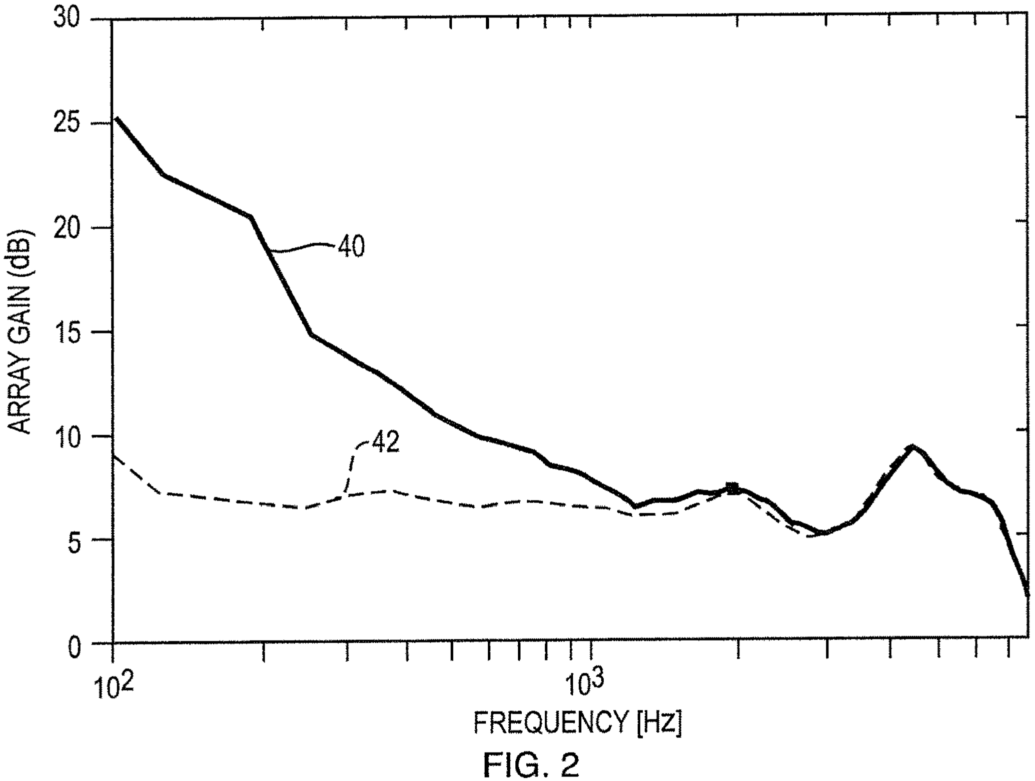
FIG. 2 is a plot of array gain vs. frequency comparing array gain of a prior art microphone array beamformer to that of an exemplary microphone array beamformer.

The array gain is indicative of the performance of a beamformer in terms of signal-to-noise ratio (SNR) as a function of frequency relative to a single array microphone. In some applications, a goal of beamformers is to maximize the array gain relative to the single microphone at the same position as the array. An MVDR beamformer is a solution to a constrained minimization problem where the constraint is undistorted signal response in the look direction (e.g., steering the microphone array toward the mouth on a headphone, or a specific look direction on a loudspeaker) while trying to minimize beamformed output energy. This maximizes the SNR for the given look direction. As non-limiting examples, goals of an MVDR beamformer can be to suppress a diffuse noise field in a diffuse noise environment, or to suppress wind noise in a windy environment; for these two cases the beamforming coefficients would be different, and would be design-specific. An example of the gain that is applied to the outputs of microphones 14 and 16 by a prior art MVDR beamformer is illustrated by plot line 40, FIG. 2. As shown, the array gain at lower frequencies is about 25 dB, the array gain begins tapering off until about 1 kHz, and then remains relatively constant (within about 5 dB) until about 10 kHz. The array gain shown in FIG. 2 is controlled via a series of beamformer coefficients or weights (W).

The beamformer coefficients or weights of the prior-art MVDR beamformer for a microphone array having at least two microphones are a function of the array geometry, the distance of the array from the source, and the coherence of the microphones in the noise field (Γ). The beamformer coefficients (W) can be calculated as set forth in equation 2.26 on page 25 of the "Superdirective Microphone Arrays" book chapter 2 that was incorporated by reference above, and reproduced immediately below as equation (1):

$$W = \frac{\Gamma_{vv}^{-1} d}{d^H \Gamma_{vv}^{-1} d} \tag{1}$$

where $\Gamma_{vv}$ is the coherence matrix as defined in equation 2.11 on page 22 of the subject book chapter 2, d is a representation of the delays and attenuation in the frequency domain as set forth in equation 2.2 on page 20 of the subject book chapter 2, and the operator $^H$ denotes a Hermitian operator. Beamforming coefficients are "complex" numbers, meaning that they have both magnitude and phase.

In practice, the sensitivities of each microphone in a multi-microphone array are not identical due to manufacturing variations and tolerances. In the present system, mismatches in sensitivity between the microphones are taken into account in the calculation of modified MVDR beamformer coefficients. In the case of an N-microphone array, where γ is the respective microphone sensitivity mismatch parameter, a modified diffuse noise coherence matrix ($\Gamma_{mm}$) is calculated as:

$$\Gamma_{mm} = \begin{bmatrix} \frac{N\gamma_1^2}{\sum_{i=1}^{N}\gamma_i^2} & \frac{N\gamma_1\gamma_2}{\sum_{i=1}^{N}\gamma_i^2}\xi_{12} & \cdots & \frac{N\gamma_1\gamma_N}{\sum_{i=1}^{N}\gamma_i^2}\xi_{1N} \\ \frac{N\gamma_1\gamma_2}{\sum_{i=1}^{N}\gamma_i^2}\xi_{12} & \frac{N\gamma_2^2}{\sum_{i=1}^{N}\gamma_i^2} & \cdots & \frac{N\gamma_2\gamma_N}{\sum_{i=1}^{N}\gamma_i^2}\xi_{2N} \\ \vdots & \vdots & \ddots & \vdots \\ \frac{N\gamma_1\gamma_N}{\sum_{i=1}^{N}\gamma_i^2}\xi_{1N} & \frac{N\gamma_2\gamma_N}{\sum_{i=1}^{N}\gamma_i^2}\xi_{2N} & \cdots & \frac{N\gamma_N^2}{\sum_{i=1}^{N}\gamma_i^2} \end{bmatrix} \tag{2}$$

This reduces for two microphones (N=2) to:

$$\Gamma_{mm} = \begin{bmatrix} \frac{2\gamma_1^2}{\gamma_1^2+\gamma_2^2} & \frac{2\gamma_1\gamma_2}{\gamma_1^2+\gamma_2^2}\xi_{12} \\ \frac{2\gamma_1\gamma_2}{\gamma_1^2+\gamma_2^2}\xi_{12} & \frac{2\gamma_2^2}{\gamma_1^2+\gamma_2^2} \end{bmatrix} \tag{3}$$

The term $\xi_{ij}$ is the complex coherence function which is for spherically isotropic noise and omnidirectional receivers given with:

$$\xi_{ij} = \frac{\sin(kr)}{kr}$$

Where k is the wavenumber and r is the distance between the microphones as set forth in equation 4.14 on page 66 of the "Superdirective Microphone Arrays" book chapter 4 that was incorporated by reference above, and reproduced immediately above. Additionally, similarly as in the reference book, the coherence matrix is normalized to have a trace equal to the number of microphones in the array.

Derivation of the diffuse noise coherence matrix format differs from the derivation in the referenced book chapters by taking into an account a mis-match between the microphones. A new signal model for an N microphone array system is given in equation 4 set-forth below (which corresponds to equation 2.2, page 20 of the book chapter 2 reference):

$$X_1(\omega) = \gamma_1(\omega)S(\omega)d_1(\omega) + \gamma_1(\omega)\upsilon_1(\omega) \quad (4)$$
$$X_2(\omega) = \gamma_2(\omega)S(\omega)d_2(\omega) + \gamma_2(\omega)\upsilon_2(\omega)$$
$$\vdots$$
$$X_N(\omega) = \gamma_N(\omega)S(\omega)d_N(\omega) + \gamma_N(\omega)\upsilon_N(\omega)$$

Where $v_i(\omega)$ is the spatial noise at the microphone (fig. 2.1, book reference, page 20). Mismatch between the microphones is modeled as a frequency dependent modulation of the signal received at each microphone and applies to both signal and noise components of the surrounding field. Mismatch can be complex, meaning that it could have a phase component specifying that the mismatch could cause a signal delay. However, for the present beamformer design this value is real, meaning that only gain and no delay is applied. Utilizing the model in Eq. 4 under the assumption of the spherically isotropic field (reference book, section 4.3, page 66) we derive the modified diffuse noise coherence matrix in Eq. 2. Using that result we can calculate a new set of beamforming coefficients that reflect correction of the diffuse noise coherence matrix:

$$W = \frac{\Gamma_{mm}^{-1} d}{d^H \Gamma_{mm}^{-1} d} \quad (5)$$

The microphone sensitivity mismatch parameter (γ) can be estimated based on the particular microphones used in the microphone array, spacing between pairs of microphones, and acceptable variability after calibration of an array in production. The environmental drift of the microphones can be measured; this can be for the particular microphones used in the microphone array, or for the types of microphones or the microphone manufacturer, more generally. The mismatch data end points can be used to run simulations that can be used to optimize over the outputs to obtain an acceptable tradeoff between array gain and protection against microphone mismatch and drift. The resulting microphone sensitivity mismatch parameters (γ) are estimated to be between about 0.1 dB and about 0.3 dB, and possibly up to about 1 dB.

Figure 3:
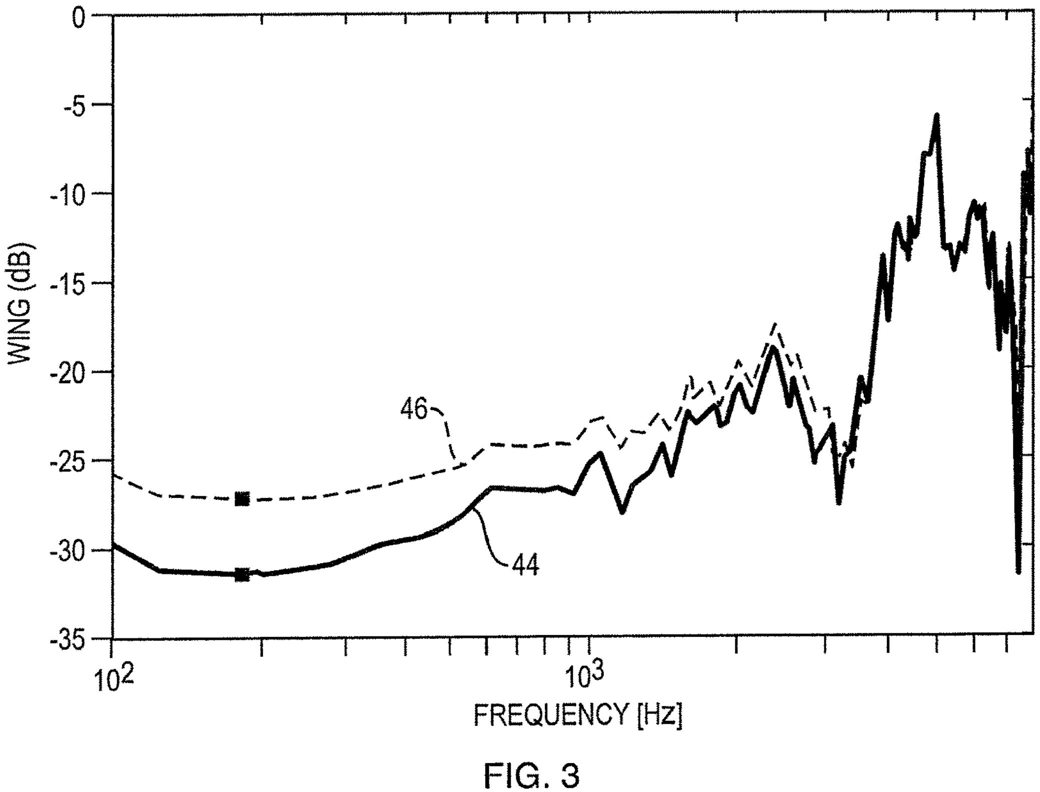
FIG. 3 is a plot of white noise gain (WNG) vs. frequency comparing the WNG of a prior art microphone array beamformer to that of the exemplary microphone array beamformer.

A result of using MVDR beamformer coefficients modified as described above, is illustrated in FIGS. 2 and 3. FIG. 2 is a plot of gain vs. frequency comparing a prior art microphone beamformer (MVDR) gain (plot line 40) to the present modified MVDR microphone array beamformer (plot line 42), using an exemplary microphone array. FIG. 3 is a plot of white noise gain vs. frequency comparing the array white noise gain of the same prior-art MVDR beamformer (plot line 44) to the modified MVDR microphone array beamformer used to calculate the data of plot line 42, FIG. 2 (plot line 46). For the calculation of the modified MVDR beamformer coefficients, the microphone mismatch parameter $\gamma_1$ was set at 0 dB, and $\gamma_2$ was set at 0.225 dB. Note that negative values of WNG as set forth in FIG. 3 represent an undesirable amplification of white noise.

FIGS. 2 and 3 establish that at frequencies from about 250 Hz (which is around the lowest frequency of concern in speech processing, as there is little energy below this frequency) to about 400-500 Hz, white noise gain is reduced by about 4 dB when using the present modified MVDR microphone array beamformer compared to the prior-art MVDR beamformer. White noise gain continues to be reduced for the present modified MVDR beamformer at frequencies ranging from about 500 Hz to about 1.2 kHz. Array gain for the modified MVDR beamformer is reduced compared to the prior-art MVDR beamformer, but only at lower frequencies. The modified MVDR beamformer exhibits little to no gain reduction at about 2,000 Hz and above, where white noise is at lower levels of about 20 dB. The point on FIG. 3 where the original WNG and the reduced WNG match can be controlled by selection of the microphone mismatch parameters.

The present modified beamformer technique can be applied to arrays of more than two microphones, as would be apparent to one skilled in the art from the above equations.

Figure 4:
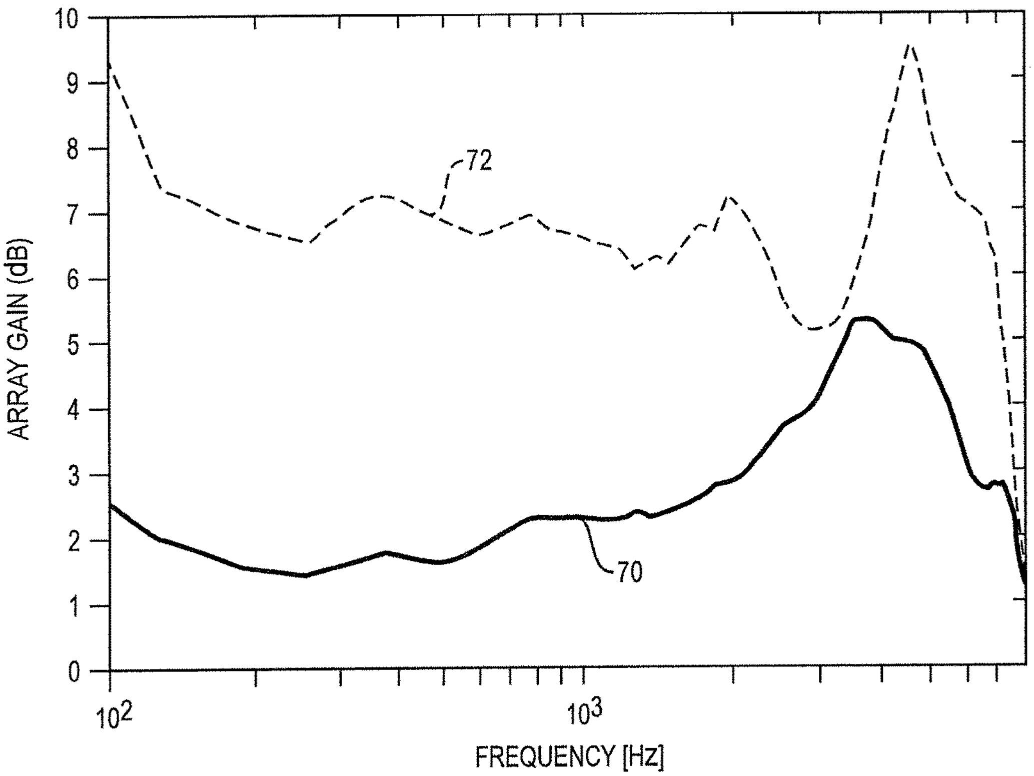
FIG. 4 is a plot of array gain vs. frequency comparing array gain of another prior art microphone array beamformer to that of an exemplary microphone array beamformer.
Figure 5:
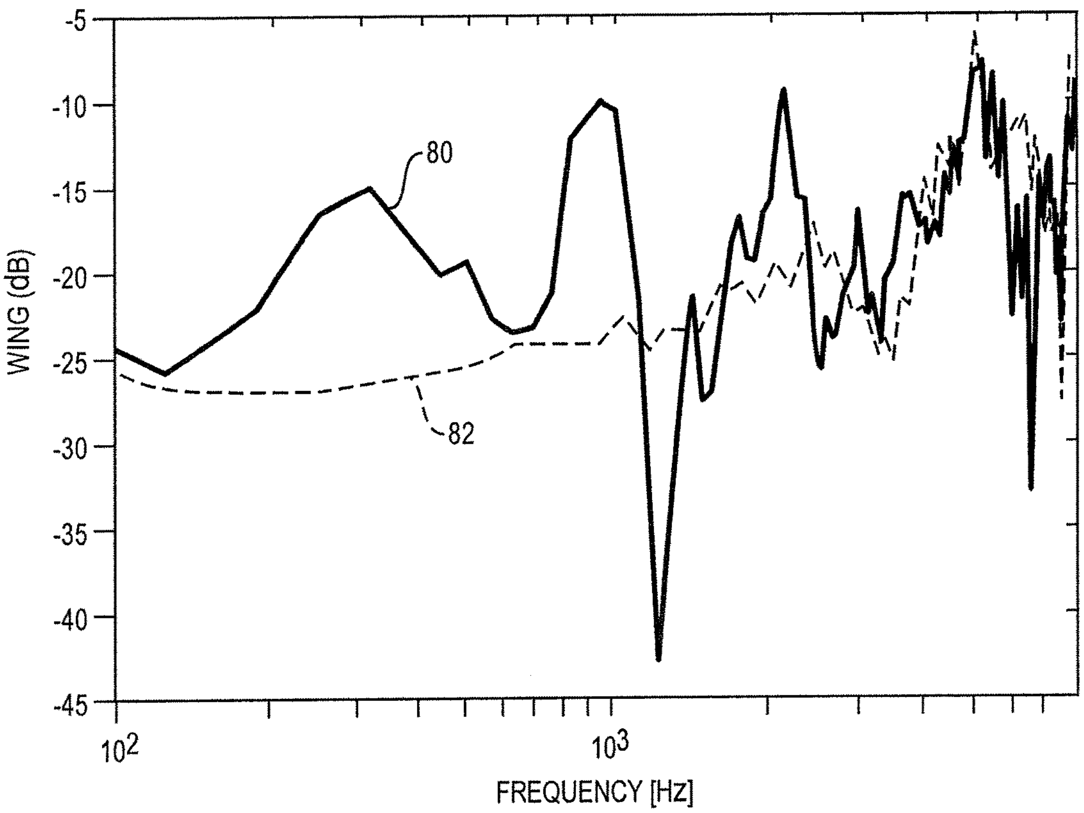
FIG. 5 is a plot of WNG vs. frequency comparing WNG of another prior art microphone array beamformer to that of the exemplary microphone array beamformer.

FIGS. 4 and 5 are plots of array gain and WNG, respectively, comparing examples of the present beamforming to the prior art, similar to the plots of FIGS. 2 and 3. Plot line 70, FIG. 4, plots array gain for a prior-art MVDR beamformer calculated using a constrained WNG, as set forth in equation 2.33 on page 28 of the book chapter 2 incorporated by reference herein, where the added scalar value (mu) was set at $0.8e^{-5}$ (or about −100 dB). Plot line 72 is equivalent to plot line 42, FIG. 2, where the present modified MVDR beamformer weights were calculated using a mismatch of 0.225 dB. The array gain is substantially increased across almost the entirety of the frequency range from 100 Hz to 7 kHz. FIG. 5 plots WNG, with plot line 80 representing the same prior art beamformer of plot line 70, FIG. 4, and plot line 82 representing the same modified beamformer of plot line 72, FIG. 4. In the case illustrated here, where the array can benefit from a WNG reduction, note that the literature-recommended offloading method (plot lines 70 and 80) creates large deviations in the array gain and WNG, even when using a very small mu of about 0.8e−5. On the other hand, employing the present beamforming system and methodology provides for a more controllable tuning parameter or mismatch (here, established as 0.225 dB), that allows an audio device designer to better tune/control the tradeoff between the WNG and SNR.

Another approach to determining the modified beamformer coefficients of the present disclosure is to establish a desired maximum white noise gain, and then determine, using the above equations, the microphone sensitivity mismatch parameters.

The present system, and the beamformer used in the system, can be applied to many beamforming methodologies, including adaptive and non-adaptive beamforming methodologies. Also, it can be applied to both near-field and far-field beamformers. Further, the beamformer modification approaches described herein can be used in Superdirective beamformers such as linearly constrained minimum variance (LCMV) beamformer and MVDR beamformers, as well as other coherence-based beamformers.

Figure 6:
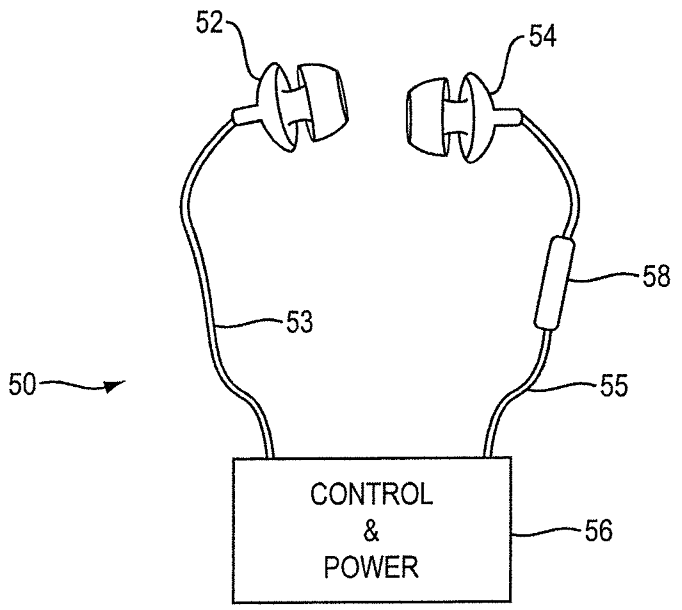
FIG. 6 is a schematic diagram of headphones that include the exemplary microphone array beamformer.

FIG. 6 is a schematic diagram of headset 50 that includes the present system and the present microphone array beamformer. In one example, earbuds 52 and 54 are fed audio signals from control and power module 56 over wires 53 and 55. Active element 58 includes the microphone array that is beamformed. Active element 58 may be used to pick up the user's voice via the microphone array, and may also include user interface elements to control aspects such as volume control and switching between functions of the wireless-connected audio source, such as a smartphone (not shown), with which headset 50 is operatively, wirelessly, connected, so that the user can make or receive phone calls or listen to music, for example. While FIG. 6 shows an example where earbuds 52 and 54 are connected to a control and power module via wires, in some examples, earbuds 52 and 54 could be completely wireless, with no tether between them.

The present system and beamformers can be used in other types of audio devices that have an array of two or more microphones that can be used to detect a user's voice. For example, other types of headphone form factors, such as those with on-ear or around-ear earcups (in which, typically, the microphones of the microphone array are on the earcups), or headphones with the microphones on the neckband, can employ the present modified beamformer. Also, the modified beamformer can be used with portable speakers, smart speakers, and home theater systems, to name several non-limiting examples of hardware platforms that can include microphone arrays and can use the present modified beamformer.

Elements of figures are shown and described as discrete elements in a block diagram. These may be implemented as one or more of analog circuitry or digital circuitry. Alternatively, or additionally, they may be implemented with one or more microprocessors executing software instructions. The software instructions can include digital signal processing instructions. Operations may be performed by analog circuitry, or by a microprocessor executing software that performs the equivalent of the analog operation. Signal lines may be implemented as discrete analog or digital signal lines, as a discrete digital signal line with appropriate signal processing that is able to process separate signals, and/or as elements of a wireless communication system.

When processes are represented or implied in the block diagram, the steps may be performed by one element or a plurality of elements. The steps may be performed together or at different times. The elements that perform the activities may be physically the same or proximate one another, or may be physically separate. One element may perform the actions of more than one block. Audio signals may be encoded or not, and may be transmitted in either digital or analog form. Conventional audio signal processing equipment and operations are in some cases omitted from the drawing.

Embodiments of the systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, floppy disks, hard disks, optical disks, Flash ROMS, nonvolatile ROM, and RAM. Furthermore, it should be understood by one of skill in the art that the computer-executable instructions may be executed on a variety of processors such as, for example, microprocessors, digital signal processors, gate arrays, etc. For ease of exposition, not every step or element of the systems and methods described above is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the disclosure.

A number of implementations have been described. Nevertheless, it will be understood that additional modifications may be made without departing from the scope of the inventive concepts described herein, and, accordingly, other embodiments are within the scope of the following claims.

What is claimed is:

1. A system, comprising:

a microphone array comprising a plurality of microphones positioned at different locations, where the microphones output microphone signals; and a beamformer that is applied to the microphone output signals and is configured to control a gain that is applied to the microphone output signals, where the gain is frequency dependent and is related to a mismatch in sensitivity between two or more of the microphones, wherein the beamformer is configured to limit the gain that is applied to the microphone output signals at input frequencies below a cutoff frequency of 2000 Hz.

2. The system of claim 1, wherein the microphones are part of headphones.

3. The system of claim 2, wherein the headphones comprise an in-ear headset and wherein the microphones are constructed and arranged to detect a sound field that is external to the headset.

4. The system of claim 1, wherein the beamformer does not limit the gain that is applied to the microphone output signals at input frequencies above the cutoff frequency.

5. The system of claim 1, wherein the gain contributes to microphone white noise gain, and wherein the limited gain results in a reduction of white noise gain.

6. The system of claim 5, wherein the white noise gain reduction is at least 4 dB over a range of input frequencies.

7. The system of claim 6, wherein the range of input frequencies is up to 300 Hz.

8. The system of claim 1, wherein the beamformer is super-directive.

9. The system of claim 1, wherein the beamformer is characterized by a plurality of frequency domain coefficients.

10. The system of claim 9, wherein the frequency domain coefficients are based on at least one of a coherence function of a diffuse noise field and a power spectral density matrix of a non-diffuse noise field.

11. The system of claim 10, wherein the coherence function is based on microphone sensitivity mismatch parameters of the microphones of the array.

12. The system of claim 11, wherein the microphone sensitivity mismatch parameters are between approximately 0.1 dB and approximately 0.3 dB.

13. The system of claim 1, wherein the beamformer is either a near-field beamformer or a far-field beamformer.

14. The system of claim 1, wherein the beamformer is a minimum variance distortionless response (MVDR) beamformer.

15. The system of claim 1, wherein the microphone sensitivity mismatch is between approximately 0.1 dB and approximately 0.3 dB.

16. The system of claim 1, wherein the cutoff frequency is 2000 Hz.

17. The system of claim 4, wherein the cutoff frequency is 2000 Hz.

18. The system of claim 1, wherein the cutoff frequency is at least 1000 Hz.

19. A system, comprising:

a microphone array comprising a plurality of microphones positioned at different locations, where the microphones output microphone signals; and a minimum variance distortionless response (MVDR) beamformer that is applied to the microphone output signals and is configured to control a gain that is applied to the microphone output signals, where the gain is frequency dependent and is related to a mismatch in sensitivity between two or more of the microphones, wherein the beamformer is configured to limit the gain that is applied to the microphone output signals at input frequencies below a cutoff frequency of 2000 Hz, and wherein the beamformer does not limit the gain that is applied to the microphone output signals at input frequencies above the cutoff frequency, wherein the gain contributes to microphone white noise gain, and wherein the reduced gain results in a reduction of white noise gain, wherein the white noise gain reduction is at least 4 dB over input frequencies of up to 300 Hz.

* * * * *